United States Patent [19]

Dumbeck

[11] Patent Number: 4,868,546

[45] Date of Patent: Sep. 19, 1989

[54] RADON DETECTOR

[76] Inventor: Robert F. Dumbeck, P.O. Box 548, Elgin, Tex. 78621

[21] Appl. No.: 905,121

[22] Filed: Sep. 9, 1986

Related U.S. Application Data

[63] Continuation-in-part of Ser. No. 657,185, Oct. 3, 1984.

[51] Int. Cl.⁴ ............................................. G08B 21/00
[52] U.S. Cl. .................................. 340/632; 250/381; 250/385.1; 73/23; 324/469
[58] Field of Search ............... 340/629, 632, 633, 634; 73/23; 324/469, 464; 250/379, 381, 385, 385.1

[56] References Cited

U.S. PATENT DOCUMENTS

| | | |
|---|---|---|
| 2,579,352 | 12/1951 | White . |
| 3,460,125 | 8/1969 | Liebermann et al. . |
| 3,851,520 | 12/1974 | Schluter et al. ............... 73/1 G X |
| 4,075,550 | 2/1978 | Castleman et al. ........... 73/861.09 X |
| 4,090,308 | 5/1978 | Stuck . |
| 4,164,172 | 8/1979 | Anderten et al. ............. 98/33 R |
| 4,250,737 | 2/1981 | Biglin ............................ 73/23 |
| 4,256,985 | 3/1981 | Goodson et al. ............... 73/23 X |
| 4,270,123 | 5/1981 | Collard ........................... 340/629 |
| 4,288,749 | 9/1981 | Martin .......................... 324/464 |
| 4,443,791 | 4/1984 | Risgin et al. ................... 340/634 |
| 4,534,775 | 8/1985 | Frazier . |
| 4,644,333 | 2/1987 | Barendsz et al. ............. 73/23 X |

*Primary Examiner*—Joseph A. Orsino
*Assistant Examiner*—Jeffery A. Hofsass
*Attorney, Agent, or Firm*—Laurence R. Brown; Alfred J. Mangels

[57] ABSTRACT

A portable electronic instrument for detecting radon gas is provided by this invention. The presence of radon gas may be reliably and quantitatively measured with simple and inexpensive immediately operable in-situ detection means. Two detectors comparatively operated with respective filtered and thus uncontaminated air and inside dwelling air to be tested provide a monitoring process that can respond immediately to radon gas.

3 Claims, 3 Drawing Sheets 4,868,546

RADON DETECTOR

TECHNICAL FIELD

This invention relates to electronic contaminated air detection means and more particularly it relates to portable instruments for monitoring air quality in dwellings.

This is a continuation-in-part of my co-pending application U.S. Ser. No. 06/657,185 filed Oct. 3, 1984 for Stale Air Detection For Dwellings.

BACKGROUND ART

Particularly in view of the backlash of increased energy costs resulting in a concentrated education process in recent years that dwellings should be well insulated with air leakages sealed about fireplaces, doors, windows, electrical wiring, keyholes, etc., it has not been uncommon to encounter asphyxia after expenditure of available oxygen within such dwellings to unsafe levels. This trend is even more pronounced in special housing conditions. Thus, for row or townhouses, less external house exposure to outside air further reduces the natural air replacement flow. Similarly for windowless walls such as in air conditioned complexes or in partly underground housing less air turnover may cause acute problems. Thus, it would be desirable to provide a system to monitor the oxygen level and provide control or alarm signals before dangerously low oxygen levels are encountered. However, one of the problems with installation of such systems is the oxygen detection. There are not available in the art simple, reliable, inexpensive oxygen detectors which can be available for ready installation in dwellings for detection and control of dangerously low oxygen levels.

It is also desirable in these tightly sealed dwellings that prevent rapid replacement of fresh air, that alarms may be available for other stale air conditions such as foul odors that disturb the human comfort index, even though these may not be as dangerous as the reduced oxygen levels. There are in this respect both explicit and general odor detection instruments available.

Of particular importance in considering contaminated or unsafe air levels in dwellings is the presence of radon gas. The Environmental Protection Agency has reported widespread presence of radon gas at levels unsafe for human occupancy over wide areas of the United States.

W. C. White in U.S. Pat. No. 2,579,352—Dec. 18, 1951 discloses means for detection of specific gases, vapors, smokes and other impurities in the atmosphere, and problems encountered in using ionization type detectors for quantitative measurements without fatigue, etc., are discussed. Thus, a flow of cleaning pure gas is interrupted by a flow of impure gas to be measured. However, it is not feasible with such a system to measure continuously a dwelling that may slowly pass from an acceptable oxygen level to a dangerously low oxygen level, even if this were able to detect oxygen.

At this time, there are available many inexpensive, special purpose smoke detectors operable with ionization detection. For the purpose of detecting foul odors of at least some types, thus, acceptable inexpensive detectors are available.

In general, as set forth by L. N. Liebermann et al. in U.S. Pat. No. 3,460,125—Aug. 5, 1969, ionization detectors have in the past been confined to detection of gaseous impurities, and not levels of oxygen. This particular detector has the ability to detect gases which either raise or lower the breakdown potential of a given atmosphere to an electric spark discharge. Any such instrumentation that depends upon critical high voltage discharge conditions cannot be used quantitatively because of the many influencing factors such as temperature, humidity and various uncritical gaseous conditions. This is particularly so for measuring a small slowly deteriorating change between acceptable and intolerable percentages of a given impurity.

Conductivity of high voltage sparks is measured by R. M. Stuck, U.S. Pat. No. 4,090,308—May 23, 1978 to determine the amount of ionizable matter in air flow paths. This method could not be adapted to reliably detect rather small changes in oxygen concentration of air, even if the sparking were an acceptable condition and could be inexpensively controlled for long term reliable performance without servicing.

There are no known portable detectors that can be used in-situ in a dwelling to measure contaminated air levels that are unsafe for human occupancy. Nor are there known inexpensive portable detectors providing instantaneous readout that can indicate the presence of radon gas at unsafe levels.

It is therefore an objective of this invention to produce improved instrumentation that can reliably detect air quality and determine unsafe conditions for human occupancy with reduced oxygen percentages in air, other impurities of the foul smelling type and the presence of radon gas, thereby to provide reliable and accurate instrumentation for determining air quality in dwellings.

Another objective of this invention is to provide portable instrumentation for in-situ immediate measurement of air quality in dwellings.

BRIEF DISCLOSURE OF THE INVENTION

This invention provides a simple and inexpensive electronic air quality detector which reliably and quantitatively provides an output signal designating air safety. The air quality in an air flow path through the detector is calibrated for operation in a critical range of human safety. Thus the difference between the 20.9% oxygen content ratio normal in clean ambient air and the approximately 17%, below an acceptable level for healthy human occupancy, can produce an alarm. Similarly the presence of radon above levels acceptable in human dwellings can be detected.

This detector has fast response for use in steady state or in a sampling mode condition. A momentary test condition is provided to assure operability at any sampling time. A broad band characteristic provides a stale air sensing function that roughly follows the index, including smoke, may be detected as well.

Particularly for use in monitoring the condition of air in a dwelling, two such detectors are connected in a comparison system, one receiving dwelling air flow therethrough and the other uncontaminated air so that a predetermined difference between the two signals indicating unsafe air quality in the dwelling produces an alarm.

BRIEF DESCRIPTION OF THE DRAWINGS

The nature of the invention will better be understood from the following description as referenced to the accompanying drawing, in which.

THE PREFERRED EMBODIMENTS

Figure 1:
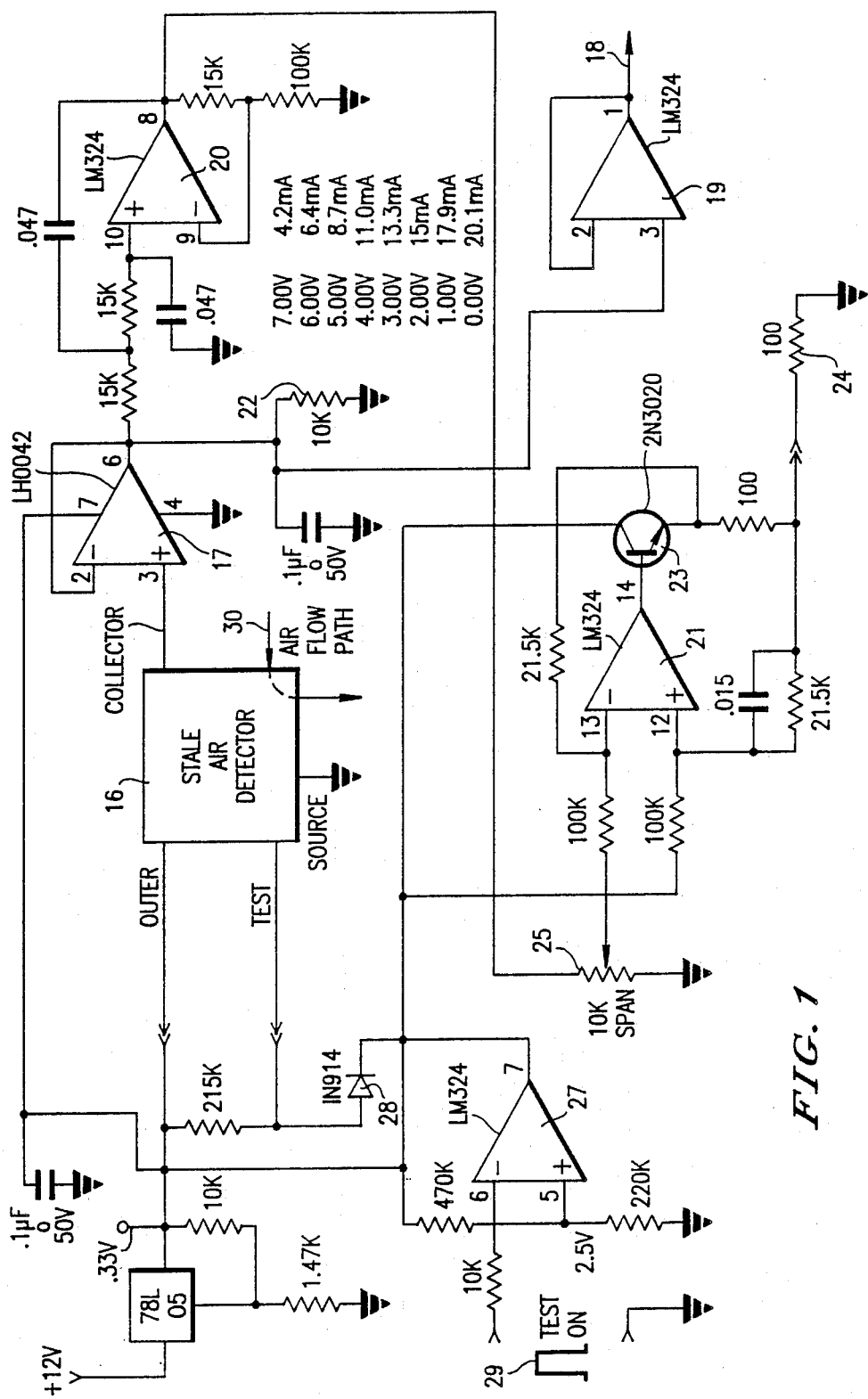
FIG. 1 is a circuit diagram, partially in block form, of a detector system afforded by this invention.
Figure 2:
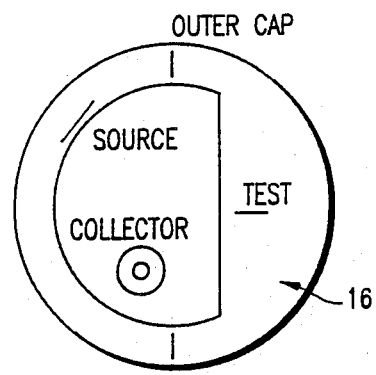
FIG. 2 is a profile view of an ionization detector element of the invention through which a stream of air being analyzed may flow.

In the diagram of FIG. 1, the typical circuit element values, voltages, and standard chip designation numbers are shown on the drawing in conventional format, except for the stale air detector 16. That element comprises a radiation driven ionization detector with a standardized micro Curie continuous radiation level derived from the self-contained isotope source AM241. Units of this type, as physically diagrammed in FIG. 2, having an inner cavity which serves as the air flow path therethrough and the various connections itemized in FIG. 1, are commercially available as model DSC.A3 from Amersham Corporation of Arlington Heights, Ill.

The present circuit is operated at an outer cap voltage of 9.33 volts as established by power supply chip 78L05. Output current from the collector is isolated at 17 by the low noise FET emitter follower which is branched two output signal paths. A first taken from the LM324 amplifier section 19 at output lead 18 is for control purposes or for comparison purposes as later described herein. The range of typical output voltages and currents at resistor 22 for corresponding signal variations in the stale air detector is set forth in the drawing table.

The remaining signal processing path through operational amplifiers 20, 21 feed the 2N3020 transistor 23 to develop the output across the constant current configuration and 100 ohm load resistor 24. A span adjust potentiometer 25 is provided and the zero adjust is established by the voltage to the outer shell of the ionization detector, and may be selected by voltage supply 78L05.

A test circuit is provided by operational amplifier 27, which by way of diode 28 will in the presence of a test signal 29 serve to produce a standardized output, such as 13 milliamperes at output resistor 24, when the circuit normally operates. This will compare with a typical clean air reading output signal of 6 milliamperes obtained by means of passing clean ambient air of normal oxygen content through the stable air detector 16 by way of path 30.

This detector system serves to produce quantitative readings as a function of the amount of oxygen percentage in the air flow path through the ionization chamber detector element 16. Furthermore, it is made sensitive to and disproportionate in response to the critical percentages of oxygen in clean air (20.9%) through the range to the percentage of oxygen unacceptable in human dwellings (19.6% or under). In general, air will not support an open candle flame with less than about 16.7% of oxygen content, at about ambient temperature (77° F.) and humidity (55%).

By comparison with commercially available oxygen analyzing equipment while varying the oxygen content of the measured air, it has thus been found that this circuit embodiment produced a set of comparative measurement points as follows when measuring air in a closed container having oxygen burned by a candle flame:

| % O$_2$ | mA |
| --- | --- |
| 20.9 | 5.9 |
| 20.1 | 9.0 |
| 19.7 | 12.7 |
| 18.3 | 13.6 |
| 17.0 | 14.0 |

In essence this forms a substantially double asymptotic exponentially shaped curve with the region between the asymptotes varying rapidly to produce the desired high sensitivity range between the normal oxygen level in ambient fresh air (20.9%) and the reduction of oxygen percentage to an unhealthy level (below 19.6%).

When the air in the box is replaced gradually by exhaled air from the human lungs, a substantially straight line characteristic is observed as the oxygen in the box decreases over the range of interest, to wit:

| % O$_2$ | mA |
| --- | --- |
| 20.8 | 5.64 |
| 20.3 | 5.72 |
| 19.9 | 5.80 |
| 19.5 | 5.83 |
| 19.0 | 5.86 |
| 18.4 | 5.89 |

When odors such as from onions are introduced with exhaled air a similar result to that of the burning candle is achieved with increased sensitivity in the critical oxygen range. Odors alone without significant oxygen change react similarly to the response to exhaled human breath.

It is clear therefore that the instrumentation provides an ionization detector and circuit arrangement therefore producing a variable signal sensitive to oxygen detection in a critical range of about 21% to 17% of air contact, and furthermore that a combination of smoke, foul odors, etc., with reduced oxygen from human breathing consumption makes the instrument readings particularly sensitive in the critical region between the normal oxygen to air ratio of 20.9% to the range of about 17% which is below an acceptable level for human occupancy. Thus, the instrument is ideal for automatic control of venting of fresh air when the oxygen level in a house falls below an acceptable value, for example.

Figure 3:
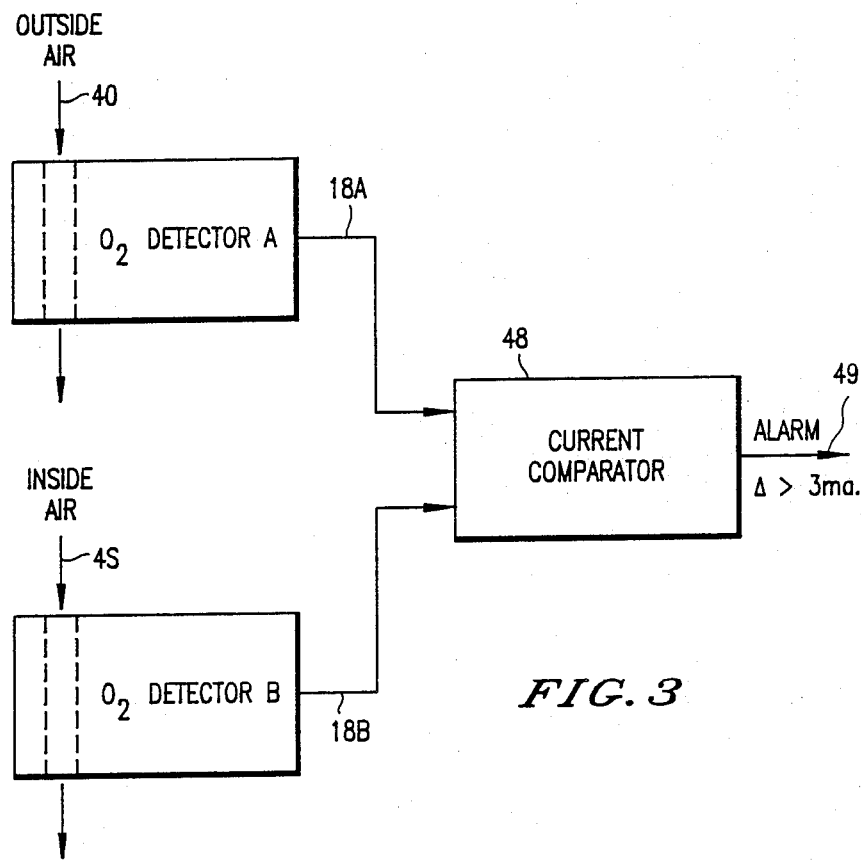
FIG. 3 is a block diagram illustrating the method of monitoring air quality in a dwelling by comparing two air flow streams, one comprising uncontaminated air and the other comprising air from the dwelling being monitored.

For constant surveillance of the air quality in a dwelling, two such stale air detector units may be coupled as shown in FIG. 3. Thus, oxygen detector unit A may receive a flow of outside clean ambient air, 40, while oxygen detector unit B receives a flow of inside air, 45, from the dwelling. A current comparator 48 then can sound an alarm at 49 (or produce a control signal) whenever the current magnitude from the inside air produces a difference greater than about three milliamperes from the clean ambient outside air, presumably with 20.9% oxygen, or reaching a level slightly above the unacceptable 19.6% oxygen level as set forth in the foregoing operational characteristic table.

Thus, the foregoing invention provides inexpensive reliable means of detecting stale air for regulating and controlling the air in a dwelling in a new and novel manner for an acceptably healthy environment.

It is noted also that the broad band capabilities of the stale air detector also substantially follows the sensitivity of the human nose to odors and will provide non-ambiguous readings fully acceptable to control of the air in a dwelling for other ionization conditions imposed by smoke, cooking and food odors and the like, which need be eliminated from the tightly sealed dwellings commonplace at present. The control of flow of fresh air into the dwelling upon detection of an alarm condition may proceed either manually or automatically from a system controlled in response to the electronic alarm output signals made available.

This detector also is sensitive to the presence of radon gas at low levels such as the four picocuries per liter of air which is set by the Environmental Protection Agency as the maximum tolerable limit for presence in dwellings to avoid significant dangers of lung cancer. The presence of radon gas is thus a factor which will result in an alarm corresponding to that of a deficiency of oxygen.

Figure 4:
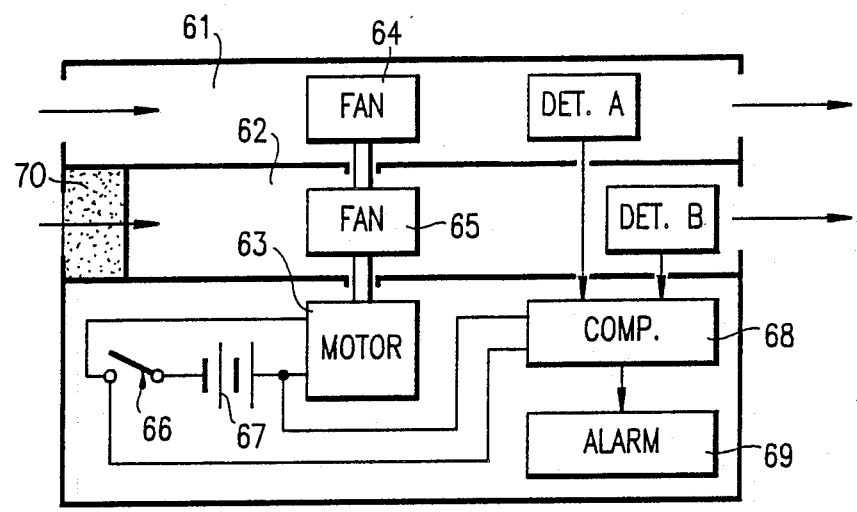
FIG. 4 is a diagrammatic sketch of a portable instrument useful in-situ in a dwelling to monitor air quality level.

It is desirable to provide a portable low cost instrument that can detect the quality of air in a dwelling and which in fact can detect the presence of radon gas, which has a tendency to accumulate in basements or areas of a dwelling close to walls or floors in contact with the earth. For this purpose, reference is made to the FIG. 4 embodiment.

The housing 60 is shown to encompass a portable air quality detector operable in the foregoing manner. It is readily within the skill of those in the art to calibrate the instrument for the presence of either deficiency of oxygen or the presence of radon at levels dangerous to human health.

Since a portable instrument for use inside a dwelling does not have access to a convenient source of outside fresh air, the air being tested flows through one channel 61, and the comparative air is filtered to provide contamination free air flowing through a second channel 62. To maintain balance, the air flow is designed to be of equal volume in both channels, so that detectors A and B will be at the same temperature in similar air flow paths and thus provide a differential reading solely from the difference in air quality in the two paths.

A single motor 63 in this respect has two rotary fan portions 64, 65 which draw air respectively through the instrument channels 61, 62 in the direction of the arrows, when switch 66 is on, as energized from battery 67. The comparator circuit 68, as hereinbefore described operates with detectors A and B to sound an alarm 69, or give a meter reading, etc.

In order to compare in-situ air with an equivalent comparative reference to the fresh atmospheric air standard hereinbefore discussed, the air in channel 62 is filtered through filter 70, which eliminates pollutants including tobacco, pollen, dust, bathroom odors, smoke, radon gas and the like. One preferable filter is obtainable from Westclox, Talley Industries division of General Time at 520 Guthridge Ct., Technology Park, Atlanta, Norcross, Ga. 30092. An acceptable filter is described in U.S. Pat. No. 4,534,775, Aug. 13, 1985 to S. E. Frazier for Air Treatment Filter Element and Air Treatment Filter. Activated charcoal will remove most pollutants including radon gas.

It may be seen therefore that the instrument calibration or meter reading will signify by the differences in air quality between channels 61 and 62 as processed through detectors A and B and Comparator 68 the quality of air inside a dwelling. Concentrations of poor quality air in basements or near underground walls, particularly if around damp areas, sump pumps or cracks in the foundation would tend to indicate the presence of radon gas. Other unsafe areas or conditions of air quality such as deficiency of oxygen are also detectable.

Figure 5:
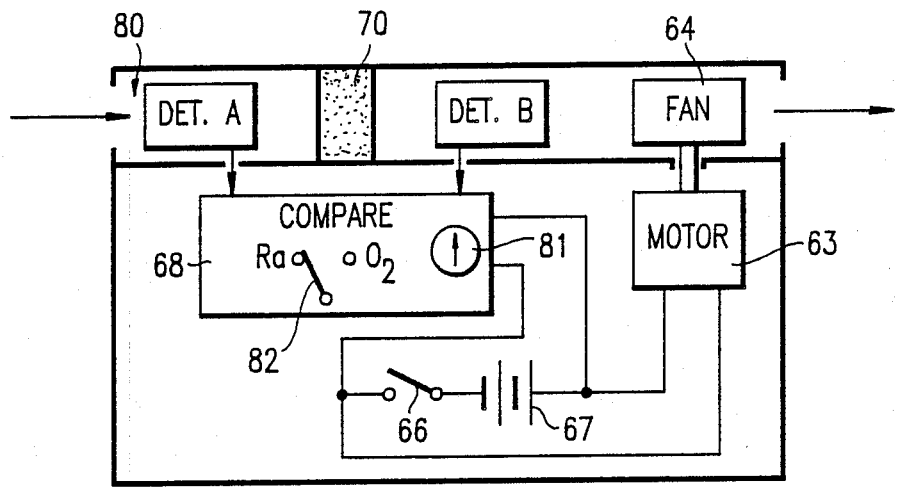
FIG. 5 is a diagrammatic sketch of a further portable air quality level instrument embodiment.

As seen in FIG. 5, the portable instrument may be simplified to have a single air flow pipe, 80 with the radon and contamination elimination filter 70 and both detector B represents a safe standard for comparison with the house ambient air passing detector A.

A meter 81 or other alarm indicator may provide a readout of the comparison signal. For detecting specifically oxygen and radon, the comparison circuit may be calibrated for proper response in either case by modifying the appropriate resistors in the FIG. 1 circuit. The respective operation mode may be selected by switch 82.

I claim:

1. A portable in-situ operable stale air detection system for monitoring the quality of air in a dwelling comprising in combination,
   two radiation driven electronic ionization detectors having a self contained standardized micro curie continuous radiation source, each operable at transistor circuit voltages, and each sensitive to the flow of air thereby for indicating by an electronic signal derived from the ionization level the percentage of ionization affecting contamination in the air flowing by the respective detector,
   blower means coupled to pass air by each of said detectors through respective air channelling means,
   first said channelling means for passing contamination free air by a first said detectors,
   second said channelling means for passing in-situ air from a dwelling to be monitored by a further one of said detectors,
   signal comparison means for comparing the signals from the two detectors to produce a comparison signal whenever poor air quality in the dwelling is signified by a predetermined difference in ionization levels of the two detectors and
   circuit operating means responsive to detected ionization changes in the signal comparison means responsive to radon gas levels in the order of four pico curies per liter of air and above to produce an alarm indication.

2. A detection system as defined in claim 1, further comprising,
   alarm indication means responsive to quantitative variations in radon concentration in the air being monitored for producing quantitative measurements of radon concentration.

3. An air contamination detection system comprising in combination,
   a pair of radiation driven electronic ioinization detectors, each having a self-contained standardized micro curie continuous radiation source and being operable to detect ionization levels in a flow of air past the detectors when powered by low operating voltages used with transistorized circuits, air channelling means for passing air of differing constituencies in respective flow paths past the respective detectors for measuring the ionization characterisitics of the air in the respective paths with one flow path passing air free from any substantial radon contamination and the other flow path passing air to be monitored for radon contamination, and transistorized signal comparison means coupled to the detectors with circuit construction enabling response to on line differences of ionization in the tow detectors at a sensitivity sufficient to produce a signal indicating the differences in air quality in the two paths caused by the magnitude of radon air contamination in the air flow path being monitored with signal magnitude variations proportional to radon concentration levels from those of the order of four pico curies per liter of air.

* * * * *